United States Patent
Shiiya

(10) Patent No.: US 11,957,896 B2
(45) Date of Patent: Apr. 16, 2024

(54) INTRAESOPHAGEAL ELECTROSTIMULATOR

(71) Applicant: NATIONAL UNIVERSITY CORPORATION HAMAMATSU UNIVERSITY SCHOOL OF MEDICINE, Hamamatsu (JP)

(72) Inventor: Norihiko Shiiya, Hamamatsu (JP)

(73) Assignee: Hamamatsu University School of Medicine, Shizuoka (JP)

( * ) Notice: Subject to any disclaimer, the term of this patent is extended or adjusted under 35 U.S.C. 154(b) by 0 days.

(21) Appl. No.: 18/265,446

(22) PCT Filed: Dec. 9, 2021

(86) PCT No.: PCT/JP2021/045338
§ 371 (c)(1),
(2) Date: Jun. 6, 2023

(87) PCT Pub. No.: WO2022/131126
PCT Pub. Date: Jun. 23, 2022

(65) Prior Publication Data
US 2023/0390549 A1    Dec. 7, 2023

(30) Foreign Application Priority Data
Dec. 18, 2020  (JP) ................................ 2020-210349

(51) Int. Cl.
*A61N 1/05*  (2006.01)
*A61N 1/36*  (2006.01)
(Continued)

(52) U.S. Cl.
CPC ....... *A61N 1/0517* (2013.01); *A61N 1/36062* (2017.08); *A61N 1/3756* (2013.01); *A61N 1/3787* (2013.01)

(58) Field of Classification Search
CPC ............ A61N 1/0517; A61N 13/36062; A61N 1/3756; A61N 1/3787
See application file for complete search history.

(56) References Cited

U.S. PATENT DOCUMENTS

| 6,325,800 B1 | 12/2001 | Durgin et al. |
| 2008/0177190 A1 | 7/2008 | Libbus et al. |

(Continued)

FOREIGN PATENT DOCUMENTS

| JP | 2002511302 A | 4/2002 |
| JP | 2012200558 A | 10/2012 |

(Continued)

OTHER PUBLICATIONS

International Search Report (ISR) dated Mar. 1, 2022 filed in PCT/JP2021/045338.

(Continued)

*Primary Examiner* — Eric D. Bertram
(74) *Attorney, Agent, or Firm* — RANKIN, HILL & CLARK LLP

(57) ABSTRACT

Provided is an intraesophageal electrostimulator configured so that other medical tools can also be easily inserted into an esophagus and misalignment in the esophagus can be reduced. An intraesophageal electrostimulator 100 includes a stimulator body 101, stimulating electrodes 111, 112, and power feed lines 113, 114. The stimulator body 101 is formed, in order to insert the stimulator body 101 into an esophagus S, in an elongated flat plate shape with flexibility in a longitudinal direction. The stimulator body 101 includes a first flat plate member 102, a second flat plate member 103, and an exterior body 104. On one plate surface of the first flat plate member 102, each of the stimulating electrodes 111, 112 is provided so as to protrude from the plate surface. The second flat plate member 103 overlaps with the other plate surface of the first flat plate member 102 such that the (Continued)

second flat plate member 103 and the first flat plate member 102 sandwich the power feed lines 113, 114. The exterior body 104 covers the first flat plate member 102 and the second flat plate member 103 overlapping with each other.

13 Claims, 3 Drawing Sheets

(51) Int. Cl.
*A61N 1/375* (2006.01)
*A61N 1/378* (2006.01)

(56) References Cited

U.S. PATENT DOCUMENTS

| | | | |
|---|---|---|---|
| 2009/0259274 A1* | 10/2009 | Simon | A61N 1/0517 607/42 |
| 2013/0006323 A1 | 1/2013 | Tal et al. | |
| 2014/0238175 A1* | 8/2014 | Huszar | A61M 25/0074 74/490.02 |
| 2015/0051450 A1 | 2/2015 | Mittal et al. | |
| 2017/0238834 A1 | 8/2017 | Kawabata et al. | |
| 2019/0038894 A1 | 2/2019 | Bassi et al. | |
| 2020/0261024 A1* | 8/2020 | Heinke | A61N 1/3614 |

FOREIGN PATENT DOCUMENTS

| | | | |
|---|---|---|---|
| JP | 2014520585 A | | 8/2014 |
| JP | 2014530644 A | | 11/2014 |
| JP | 2017000230 A | * | 1/2017 |
| JP | 2017000230 A | | 1/2017 |
| WO | 2016021633 A1 | | 2/2016 |

OTHER PUBLICATIONS

Office Action dated Jan. 25, 2023 for the corresponding Japanese Patent Application No. 2022-569926.

Decision to Grant dated Mar. 1, 2023 for the corresponding Japanese Patent Application No. 2022-569926.

* cited by examiner

INTRAESOPHAGEAL ELECTROSTIMULATOR

TECHNICAL FIELD

The present invention relates to an intraesophageal electrostimulator arranged in an esophagus to electrically stimulate an inner wall surface of the esophagus.

BACKGROUND ART

Typically, there has been known an intraesophageal electrostimulator that electrically stimulates an inner wall surface of an esophagus in order to monitor the state of a spinal cord during a surgery. For example, in a spinal cord function monitoring electrode device which is an intraesophageal electrostimulator provided with electrodes as disclosed in Patent Literature 1 below, a first electrode and a second electrode are provided on an outer surface of an elongated member having flexibility and formed in a cylindrical tube shape.

CITATION LIST

Patent Literature

PATENT LITERATURE 1: JP-A-2017-230

However, the spinal cord function monitoring electrode device described in Patent Literature 1 above includes the first electrode and the second electrode, and the elongated member to be inserted into an esophagus is formed in the cylindrical shape. Thus, it is difficult to insert other medical tools (e.g., a transesophageal echo probe) into the esophagus. In addition, there is a problem that the position of the elongated member positioned in the esophagus is easily misaligned.

The present invention copes with the above-described problems. An object of the present invention is to provide an intraesophageal electrostimulator configured so that other medical tools can be easily inserted into an esophagus and misalignment in the esophagus can also be reduced.

SUMMARY OF INVENTION

In order to achieve the object described above, a feature of the present invention is an intraesophageal electrostimulator arranged in an esophagus to electrically stimulate a spinal cord via an inner wall surface of the esophagus, including: at least one stimulating electrode that is arranged in the esophagus to electrically stimulate the inner wall surface of the esophagus; a stimulator body that is formed elongated at least with a length from a mouth to a throat and holds the stimulating electrode; and a power feed line that supplies electricity to the stimulating electrode, in which the stimulator body is formed in a flat plate shape having a length at least from the mouth to the throat, having flexibility at least in a longitudinal direction, and further having a width that expands a lumen of the esophagus outward, and the stimulating electrode is provided at a center portion in the width direction of the stimulator body.

According to the feature of the present invention configured as described above, in the intraesophageal electrostimulator, the stimulator body to be inserted into the esophagus is formed in the flat plate shape with the flexibility in such a direction that the stimulator body extends long. Thus, even in a case where other medical tools are also inserted into the esophagus, the stimulator body is less likely to physically contact the other medical tools. Consequently, the other medical tools can be easily inserted. In addition, misalignment of the position of the stimulator body in the esophagus can also be reduced.

Further, another feature of the present invention is that in the intraesophageal electrostimulator, the stimulator body has flexibility also in a width direction perpendicular to the longitudinal direction.

According to the other feature of the present invention configured as described above, in the intraesophageal electrostimulator, the stimulator body also has the flexibility in the width direction perpendicular to the longitudinal direction. Thus, insertion into the esophagus or removal from the esophagus can be smoothly performed.

Further, still another feature of the present invention is that in the intraesophageal electrostimulator, the stimulator body has flexibility at outer edge portions at both ends in the width direction.

According to still another feature of the present invention configured as described above, in the intraesophageal electrostimulator, the outer edge portions at both ends of the stimulator body in the width direction thereof have the flexibility. Thus, the outer edge portions of the stimulator body deform along the inner wall of the esophagus. Consequently, the stimulator body is easily inserted or removed. In addition, misalignment in the esophagus can be reduced.

Further, still another feature of the present invention is that in the intraesophageal electrostimulator, the stimulator body is formed such that a stiffness of an inner portion between the outer edge portions at the both ends in the width direction is higher than a stiffness of each outer edge portion.

According to still another feature of the present invention configured as described above, the intraesophageal electrostimulator is formed such that the stiffness of the inner portion between the outer edge portions at both ends of the stimulator body in the width direction thereof is higher than the stiffness of the outer edge portion. Thus, buckling (bending in the longitudinal direction) of the stimulator body when the stimulator body is inserted into the esophagus is reduced. Consequently, the stimulator body can be smoothly inserted into the esophagus.

Further, still another feature of the present invention is that in the intraesophageal electrostimulator, the stimulator body includes a first flat plate member formed in a flat plate shape, and a second flat plate member formed in a flat plate shape having a narrower width than that of the first flat plate member and overlapping with the first flat plate member.

According to still another feature of the present invention configured as described above, in the intraesophageal electrostimulator, the stimulator body includes the first flat plate member formed in the flat plate shape and the second flat plate member formed in the flat plate shape having the narrower width than the width of the first flat plate member and overlapping with the first flat plate member. Thus, the stimulator body having a higher stiffness at the inner portion between the outer edge portions at both ends of the stimulator body in the width direction thereof can be easily formed.

Further, still another feature of the present invention is that in the intraesophageal electrostimulator, the stimulator body is formed with a width decreasing toward a tip end portion.

According to still another feature of the present invention configured as described above, the intraesophageal electrostimulator is formed with the stimulator body width decreasing toward the tip end portion of the stimulator body. Thus, the stimulator body can be smoothly inserted into the esophagus.

Further, still another feature of the present invention is that in the intraesophageal electrostimulator, the power feed line is attached integrally with the stimulator body.

According to still another feature of the present invention configured as described above, in the intraesophageal electrostimulator, the power feed line is attached, without separation, integrally with the stimulator body. Thus, the stimulator body can be smoothly inserted into the esophagus. In addition, other medical tools can be easily inserted into the esophagus.

Further, still another feature of the present invention is that in the intraesophageal electrostimulator, the stimulating electrode includes at least two stimulating electrodes provided along the longitudinal direction of the stimulator body.

According to still another feature of the present invention configured as described above, in the intraesophageal electrostimulator, the stimulating electrode includes the at least two stimulating electrodes provided along the longitudinal direction of the stimulator body. Thus, electric stimulation can be performed by the positive and negative electrodes provided in the esophagus. Moreover, in the intraesophageal electrostimulator, the two or more stimulating electrodes provided along the longitudinal direction of the stimulator body can simultaneously perform electric stimulation at desired positions or multiple positions.

Further, still another feature of the present invention is that in the intraesophageal electrostimulator, the stimulating electrode protrudes from a plate surface of the stimulator body.

According to still another feature of the present invention configured as described above, in the intraesophageal electrostimulator, the stimulating electrode protrudes from the plate surface of the stimulator body. Thus, the stimulating electrode can effectively contact the inner wall surface of the esophagus.

Further, still another feature of the present invention is that in the intraesophageal electrostimulator, the stimulator body is provided with a scale along the longitudinal direction.

According to still another feature of the present invention configured as described above, in the intraesophageal electrostimulator, the stimulator body is provided with the scale along the longitudinal direction. Thus, the amount of insertion of the stimulator body into a body or the position of the stimulating electrode inserted into the body can be correctly grasped.

Further, still another feature of the present invention is that in the intraesophageal electrostimulator, the stimulating electrode is provided on a surface of the stimulator body facing a spinal cord in the esophagus.

According to still another feature of the present invention configured as described above, in the intraesophageal electrostimulator, the stimulating electrode is provided on the surface of the stimulator body facing the spinal cord in the esophagus. Thus, the spinal cord can be accurately and stably electrically stimulated.

Further, still another feature of the present invention is that in the intraesophageal electrostimulator, the stimulator body is configured such that the stimulating electrode is provided on one surface and the other surface is formed as a smooth surface.

According to still another feature of the present invention configured as described above, in the intraesophageal electrostimulator, the stimulating electrode is provided on the one surface of the stimulator body. In addition, the other surface is formed as the smooth surface. Thus, other medical tools such as an ultrasonic probe can be smoothly slid on the other surface as the smooth surface into the esophagus.

DESCRIPTION OF EMBODIMENTS

Figure 1:
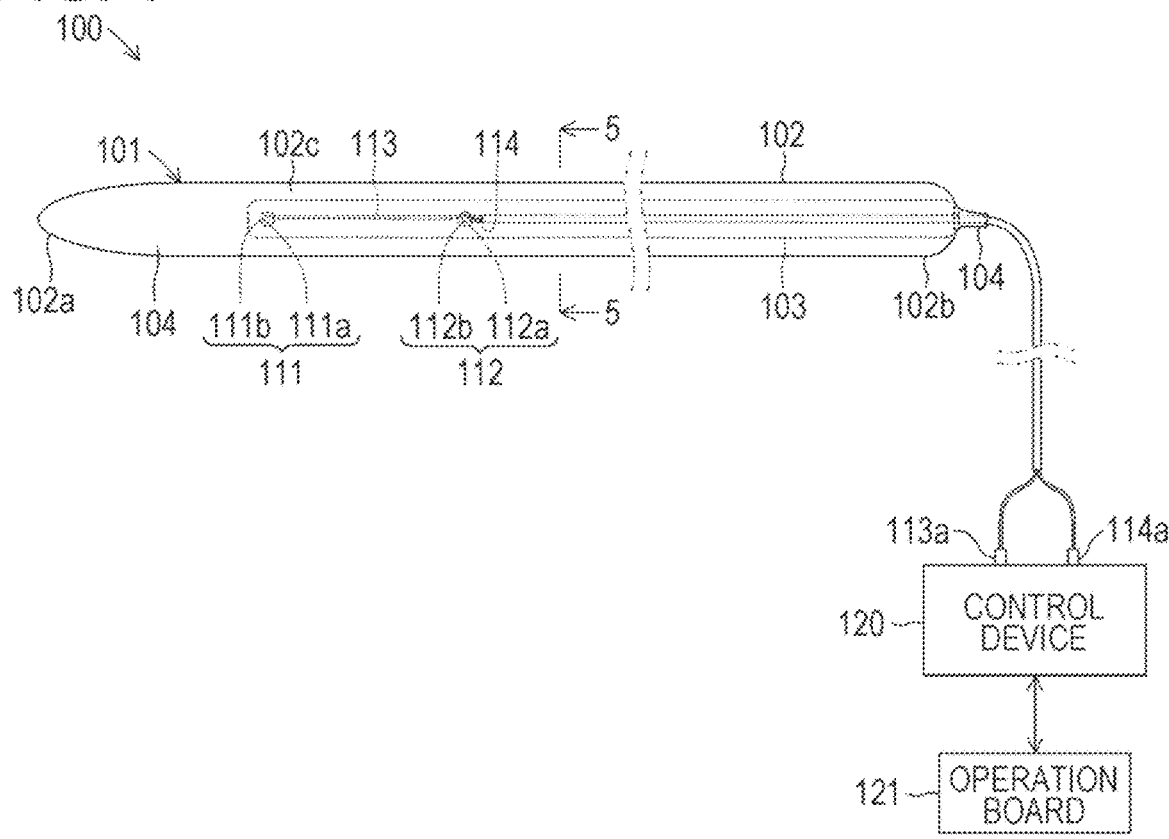
FIG. 1 is a view for describing the outline of external and system configurations of an intraesophageal electrostimulator according to one embodiment of the present invention.
Figure 2:
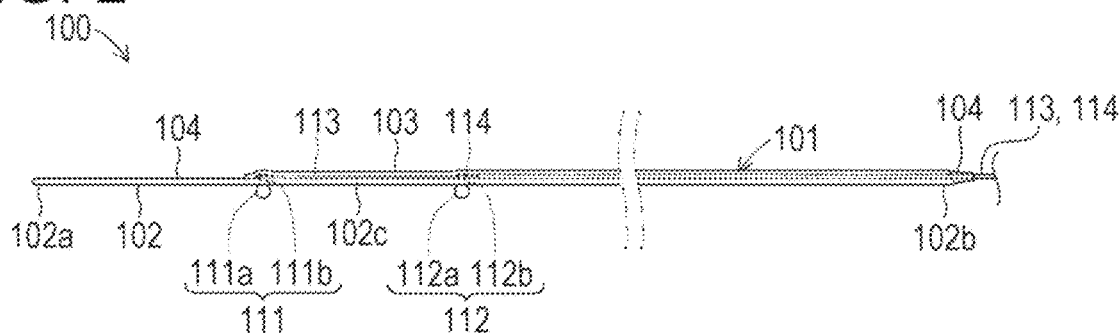
FIG. 2 is a partial side view showing, from the side, a main portion of the intraesophageal electrostimulator shown in FIG. 1.
Figure 3:
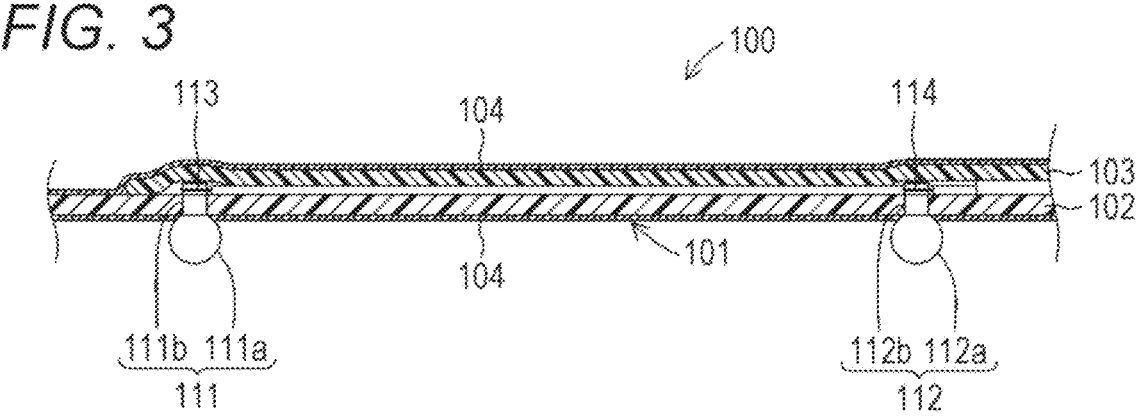
FIG. 3 is a sectional view of a main portion showing the outline of an internal configuration of the intraesophageal electrostimulator shown in FIG. 2.
Figure 4:
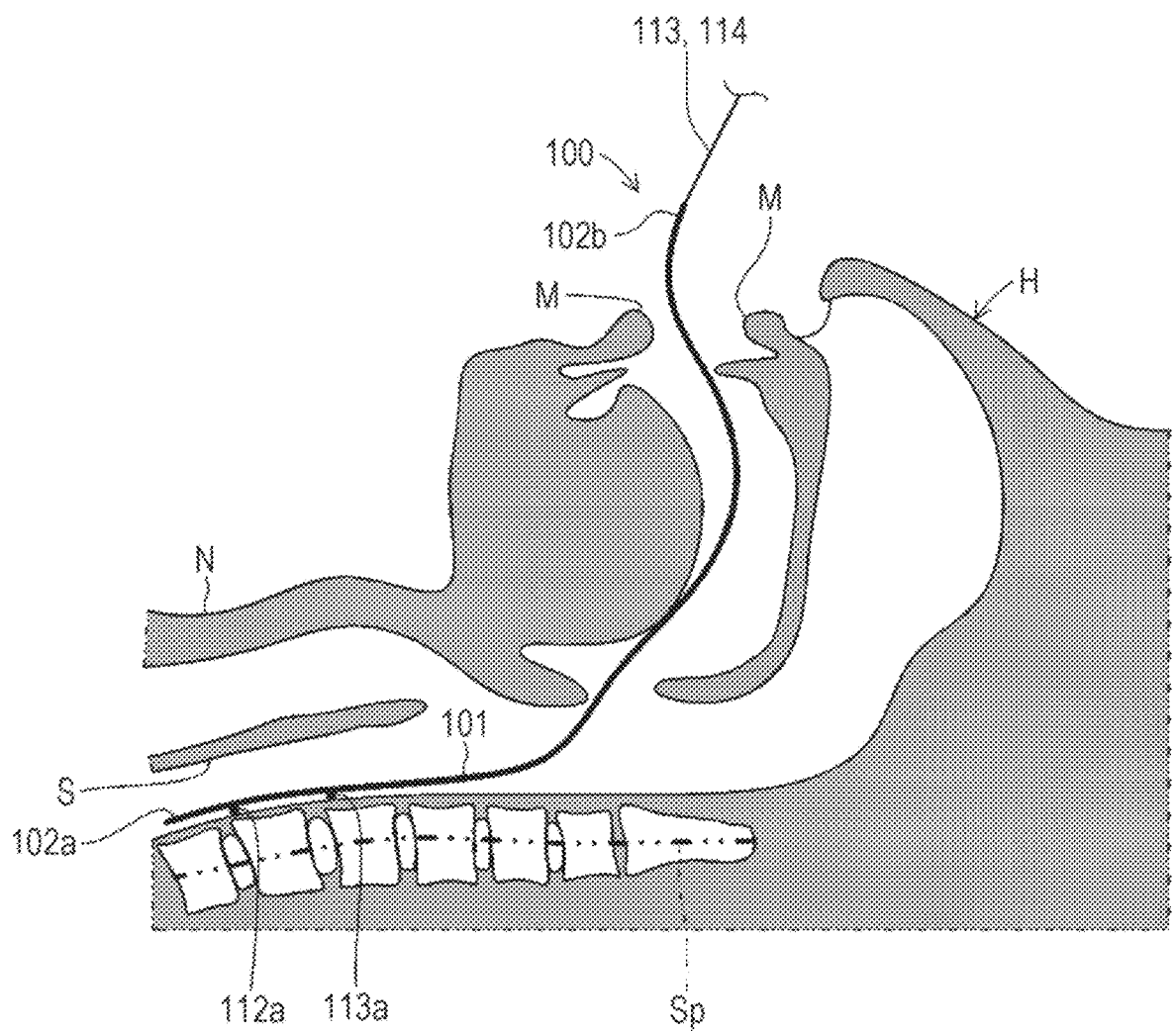
FIG. 4 is a schematic sectional view for describing a state when the intraesophageal electrostimulator shown in FIG. 1 is inserted into the esophagus of a human.

Hereinafter, one embodiment of an intraesophageal electrostimulator according to the present invention will be described with reference to the drawings. FIG. 1 is a plan view showing the outline of the entire configuration of an intraesophageal electrostimulator 100 according to the present invention. Moreover, FIG. 2 is a side view showing the outline of the entire configuration of the intraesophageal electrostimulator 100 shown in FIG. 1. Further, FIG. 3 is a sectional view of a main portion showing the outline of an internal configuration of the intraesophageal electrostimulator shown in FIG. 2. FIG. 4 is a partial sectional view of a human body schematically showing the intraesophageal electrostimulator 100 shown in FIG. 1 in a state in which the intraesophageal electrostimulator 100 is inserted into the esophagus Sofa human H.

The intraesophageal electrostimulator 100 is a tool arranged in the esophagus S of the human H to electrically stimulate the spinal cord Sp via an inner wall surface of the esophagus S. The intraesophageal electrostimulator 100 is arranged in the esophagus S to electrically stimulate the spinal cord Sp via the inner wall surface in order to monitor the presence or absence of occurrence of a spinal cord ischemic injury during a surgery for the aorta, for example. Note that in FIG. 4, the spinal cord Sp passing in the backbone is indicated by a chain double-dashed line.

(Configuration of Intraesophageal Electrostimulator 100)

The intraesophageal electrostimulator 100 includes a stimulator body 101. The stimulator body 101 is a component for arranging each of stimulating electrodes 111, 112 in the esophagus S. The stimulator body 101 is formed as an elongated body extending at least with a length from the mouth M of the human H to the arrangement position of each of the stimulating electrodes 111, 112 in the esophagus S. In this case, the stimulator body 101 has such flexibility that the stimulator body 101 is bendable in a longitudinal direction so as to elastically deform along a lumen in the body of the human H. In the present embodiment, the stimulator body 101 is formed at least with a length (about 300 mm) from the mouth M to the throat N of the human H. The stimulator body 101 mainly includes each of a first flat plate member 102, a second flat plate member 103, and an exterior body 104.

The first flat plate member 102 is a main component to be inserted along the inside of the mouth cavity and esophagus S of the human H. The first flat plate member 102 is formed in the shape of a thin plate at least with a length from the mouth M to the throat N of the human H. In this case, the first flat plate member 102 has such flexibility that the first flat plate member 102 is freely and elastically bendable in the longitudinal direction and a width direction.

In the present embodiment, the first flat plate member 102 is formed with a length of 300 mm, a width of 16 mm, and a thickness of 0.3 mm from a transparent poly carbonate material. In this case, in the present embodiment, the first flat plate member 102 is formed in a tapered shape having a width gradually decreasing toward a tip end portion 102a to be inserted into the body of the human H. Each of the tip end portion 102a of the first flat plate member 102 and a back end portion 102b opposite to the tip end portion 102a is formed in an arc shape as viewed in plane. Each of the two stimulating electrodes 111, 112 is attached to the first flat plate member 102 with exposed on a plate surface of the first flat plate member 102.

The second flat plate member 103 is a component for partially reinforcing the first flat plate member 102 to enhance the stiffness thereof and holding each of the stimulating electrodes 111, 112 and power feed lines 113, 114 together with the first flat plate member 102. The second flat plate member 103 is attached to the first flat plate member 102. More specifically, the second flat plate member 103 is a flexible thin plate having a length and a width shorter than those of the first flat plate member 102 and having a quadrangular shape as viewed in plane. In the present embodiment, the second flat plate member 103 is formed with a length of 255 mm, a width of 8 mm, and a thickness of 0.5 mm from a transparent polycarbonate material.

The second flat plate member 103 is bonded, with a not-shown adhesive, to a position closer to a back end portion 102b side with respect to the tip end portion 102a of the first flat plate member 102 at a center portion of the first flat plate member 102 in the width direction thereof. Thus, the stiffness of the portion, to which the second flat plate member 103 is bonded, of the first flat plate member 102 is reinforced.

Consequently, the stimulator body 101 is formed, as a whole, less bendable and deformable at the portion to which the second flat plate member 103 is bonded. Of the first flat plate member 102, the flexibility of an outer edge portion 102c of the portion to which the second flat plate member 103 is bonded is maintained in this case. Each of the stimulating electrodes 111, 112 and the power feed lines 113, 114 is arranged between the first flat plate member 102 and the second flat plate member 103.

The exterior body 104 is a thin film-shaped component integrally covering the first flat plate member 102 and the second flat plate member 103. In the present embodiment, the exterior body 104 is a heat-shrinkable transparent silicon rubber tube integrally covering the first flat plate member 102 and the second flat plate member 103. In this case, the exterior body 104 also covers a boundary portion with the power feed lines 113, 114 protruding from the stimulator body 101. In the present embodiment, the exterior body 104 is formed with a post-shrinkage thickness of 0.2 mm on one side. With the exterior body 104, each of the surface of the stimulator body 101 provided with the later-described stimulating electrodes 111, 112 and the opposite surface thereof is formed as a smooth surface.

The stimulating electrode 111, 112 is a component that contacts the inner wall surface of the esophagus S to electrically stimulate the inner wall surface. The stimulating electrode 111, 112 is made of a material having conductivity, such as platinum, copper, or stainless steel. The stimulating electrode 111, 112 mainly includes each of a contact portion 111a, 112a and a connection portion 111b, 112b.

The contact portion 111a, 112a is a portion that contacts the inner wall surface of the esophagus S to electrify the inner wall surface. The contact portion 111a, 112a is formed so as to protrude from the plate surface of the first flat plate member 102 opposite to the plate surface to which the second flat plate member 103 is bonded. In the present embodiment, each of the contact portions 111a, 112a is formed in a spherical shape. These contact portions 111a, 112a are provided, at a center portion of the first flat plate member 102 in the width direction thereof, with a predetermined clearance in the longitudinal direction.

In this case, the arrangement clearance between the contact portion 111a and the contact portion 112a is set as necessary according to, e.g., the size or state of the esophagus S into which the intraesophageal electrostimulator 100 is to be inserted, the state of the spinal cord Sp, the voltage or current value of the electricity to be applied, or a purpose for electricity application. In the present embodiment, the arrangement clearance between the contact portion 111a and the contact portion 112a is set to 40 mm.

The contact portion 111a provided on a tip end portion 102a side at the stimulator body 101 is arranged with a predetermined clearance from the tip end portion 102a. In this case, the predetermined clearance between the tip end portion 102a and the contact portion 111a of the stimulating electrode 111 has such a length that the first flat plate member 102 on the tip end portion 102a side with respect to the contact portion 111a can contact the wet inner wall surface of the esophagus S even while bendably deforming. This clearance is approximately 30 mm or more. In the present embodiment, the predetermined clearance between the tip end portion 102a and the contact portion 111a of the stimulating electrode 111 is set to 50 mm.

The connection portion 111b, 112b is a portion to be electrically connected to the power feed line 113, 114 to receive supplied electricity. The connection portion 111b, 112b is a circular columnar protrusion protruding from the contact portion 111a, 112a and penetrating the first flat plate member 102. Note that the connection portion 111b, 112b may be in any form as long as the power feed line 113, 114 can be electrically connected to the contact portion 111a, 112a, needless to say.

The power feed line 113, 114 is a component for supplying electricity to the stimulating electrode 111, 112. The power feed line 113, 114 is a metal wire having conductivity, such as a copper wire, and covered with an insulator such as a resin tube. These power feed lines 113, 114 may be physically separated from each other. Alternatively, the power feed lines 113, 114 may pass in one insulating tube. As another alternative, the two power feed lines 113, 114 may be twisted together into one wire, for example. One end portion of the power feed line 113 and one end portion of the power feed line 114 are connected to the stimulating electrodes 111, 112 by a connection method such as soldering. In addition, each of the other end portions is connected to a control device 120 as a power source via a connection terminal 113a, 114a.

The control device 120 includes a microcomputer having a CPU, a ROM, a RAM and the like. The control device 120 executes a not-shown control program stored in a storage device, thereby controlling operation of the intraesophageal electrostimulator 100 in an integrated manner. More specifically, the control device 120 outputs an electric signal for electrically stimulating the spinal cord Sp via the esophagus S to the power feed lines 113, 114. In this case, the electric signal is, for example, a pulse signal to be output with a constant voltage of 100 V or more and 600 V or less and a constant current of 100 mA or more and 300 mA or less at an interval of 2 ms during 0.05 ms. Note that either of the stimulating electrodes 111, 112, which are supplied with electric signals by the control device 120, may be a positive electrode or a negative electrode.

The control device 120 includes an operation board 121 having each of an input device with a switch group that receives an instruction from a user to input the instruction to the control device 120, a display lamp that displays the operation status of the control device 120, and a liquid crystal display device. Note that the control device 120 includes a power source that receives power from an external power source to supply the power to the intraesophageal electrostimulator 100, needless to say.

(Manufacturing of Intraesophageal Electrostimulator 100)

Next, a process of manufacturing the intraesophageal electrostimulator 100 will be described, First, a worker prepares each of the first flat plate member 102, the second flat plate member 103, the stimulating electrodes 111, 112, and the power feed lines 113, 114. In this case, the first flat plate member 102 and the second flat plate member 103 can be formed by injection molding with a resin material or cutting of a resin material. The stimulating electrodes 111, 112 can be formed by cutting or pressing of a metal material.

Next, the worker penetrates each of the connection portion 111b of the stimulating electrode 111 and the connection portion 112b of the stimulating electrode 112 into the first flat plate member 102, thereby attaching these portions to the first flat plate member 102. Thereafter, the worker connects the power feed line 113 to the connection portion 111b, and connects the power feed line 114 to the connection portion 111b. Next, the worker applies the adhesive to one surface of the second flat plate member 103. Thereafter, the worker bonds the second flat plate member 103 onto the first flat plate member 102 such that the connection portions 111b, 112b and the power feed lines 113, 114 on the first flat plate member 102 are covered.

Next, the worker covers, with the exterior body 104, the first flat plate member 102 to which the second flat plate member 103 is bonded. Specifically, the worker inserts the first flat plate member 102, to which the second flat plate member 103 is bonded, into the tubular silicon rubber tube which is the material of the exterior body 104, and then, heats the tube. In this manner, the first flat plate member 102 to which the second flat plate member 103 is bonded can be covered with the exterior body 104. In the above-described manner, the worker can complete the intraesophageal electrostimulator 100.

(Operation of Intraesophageal Electrostimulator 100)

Operation of the intraesophageal electrostimulator 100 configured as described above will be described. As described above, the intraesophageal electrostimulator 100 is arranged in the esophagus S in order to monitor the presence or absence of occurrence of the spinal cord ischemic injury during the surgery for the aorta. The intraesophageal electrostimulator 100 electrically stimulates the spinal cord Sp. First, the user such as a doctor or a nurse connects the connection terminals 113a, 114a of the intraesophageal electrostimulator 100 to the control device 120. Then, the user turns on the control device 120. Accordingly, the control device 120 executes the not-shown control program, and is brought into a standby state.

Next, the user inserts the stimulator body 101 through the mouth M of a patient (human H) targeted for insertion of the intraesophageal electrostimulator 100, as shown in FIG. 4. In this manner, the stimulating electrodes 111, 112 are arranged at desired positions in the esophagus S. In this case, the stimulator body 101 freely bends in the longitudinal direction. Thus, the user can insert the stimulator body 101 while bending the stimulator body 101 along the inner shape of the esophagus S. Moreover, in this case, the stimulator body 101 is formed such that the stiffness of the portion, to which the second flat plate member 103 is bonded, of the first flat plate member 102 is enhanced. Thus, frequent or unnecessary bending upon insertion is reduced.

Figure 5:
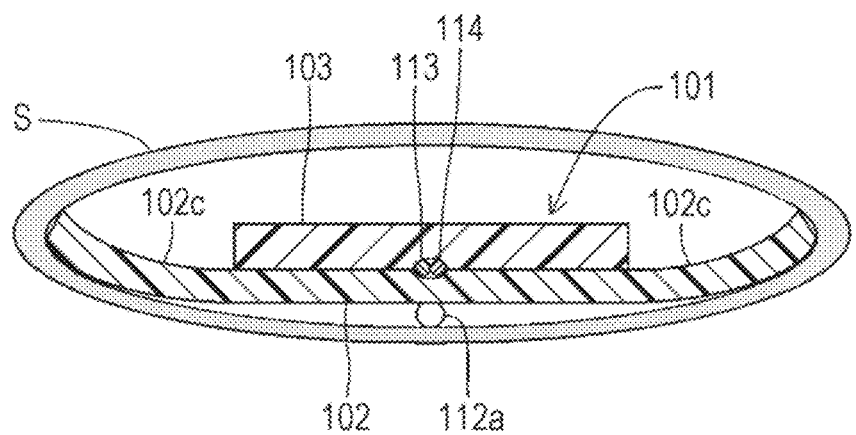
FIG. 5 is a schematic sectional view along a 5-5 line shown in FIG. 1 for describing the state of the intraesophageal electrostimulator inserted into the esophagus.

The stimulator body 101 is formed in a flat plate shape. Thus, even in a case where other medical tools are arranged in the esophagus S, the user can smoothly insert the stimulator body 101. In addition, misalignment of the positions of the other medical tools can also be reduced. As shown in FIG. 5, the intraesophageal electrostimulator 100 is inserted while expanding the inner diameter of the esophagus S in the width direction of the stimulator body 101. Thus, the inner wall surface of the esophagus S can easily closely contact the stimulating electrodes 111, 112. In this case, the outer edge portions 102c of the first flat plate member 102 in the width direction thereof bendably deforms in a curved shape along this width direction. Thus, the intraesophageal electrostimulator 100 expands the lumen of the esophagus S outward, thereby maintaining a hollow space. Note that in FIG. 5, the exterior body 104 is not shown.

Next, the user electrically stimulates the spinal cord Sp of the patient. Specifically, the user operates the control device 120 to electrically stimulate the inner wall surface of the esophagus S from the stimulating electrodes 111, 112 of the intraesophageal electrostimulator 100. Accordingly, the user can electrically stimulate the spinal cord Sp via the esophagus S. In this case, when electrically stimulating the spinal cord Sp, the user can separately attach, to the patient, an evoked potential detection device (not shown) that records an electricity evoked from the spinal cord Sp. With this configuration, an evoked potential when the spinal cord Sp is electrically stimulated can be detected. In this manner, the presence or absence of occurrence of the spinal cord ischemic injury can be monitored.

Moreover, in this case, if the stimulating electrodes 111, 112 do not correctly contact the inner wall surface of the esophagus S, the user can turn the stimulator body 101 in the longitudinal direction or about the axis in the longitudinal direction. In this manner, the positions or orientations of the stimulating electrodes 111, 112 can be adjusted such that the stimulating electrodes 111, 112 closely contact the inner wall surface of the esophagus S. The stimulator body 101 is formed in the flat plate shape. Thus, in a case where other medical tools such as a transesophageal echo probe are inserted into the esophagus S, the user can smoothly insert the other medical tools. In addition, misalignment of the position of the stimulator body 101 can also be reduced.

Next, when the stimulator body 101 is removed from the esophagus S, the user operates the control device 120 to interrupt electric stimulation by the stimulating electrodes 111, 112. Thereafter, the stimulator body 101 is removed from the esophagus S. In this manner, the user can remove the stimulator body 101 from the esophagus S. In this case, the stimulator body 101 is formed in the flat plate shape. Thus, even in a case where other medical tools are arranged in the esophagus S, the user can smoothly remove the stimulator body 101. In addition, misalignment of the positions of the other medical tools can also be reduced.

Next, the user detaches the connection terminals 113a, 114a of the intraesophageal electrostimulator 100 from the control device 120, and ends the process.

As can be understood from operation described above, according to the above-described embodiment, the intraesophageal electrostimulator 100 is formed in the flat plate shape with the flexibility in such a direction that the stimulator body 101 inserted in the esophagus S extends long. Thus, even in a case where other medical tools are also inserted into the esophagus S, physical contact is less likely to be caused. Consequently, the other medical tools can be easily inserted. In addition, misalignment of the position of the stimulator body 101 in the esophagus S can also be reduced.

Further, the embodiments of the present invention are not limited to the above-described embodiment. Various modifications can be made without departing from the object of the present invention, Note that in each of modifications described below, corresponding reference numerals are used to represent components similar to those of the above-described embodiment. Moreover, description thereof will be omitted.

For example, in the above-described embodiment, the intraesophageal electrostimulator 100 includes the two stimulating electrodes 111, 112. However, the intraesophageal electrostimulator 100 may include at least one stimulating electrode. In a case where the intraesophageal electrostimulator 100 includes the one stimulating electrode, the user can provide, for the patient, an electrode that provides a potential with the polarity opposite to that of a potential provided to the stimulating electrode included in the intraesophageal electrostimulator 100. In this manner, the spinal cord Sp can be directly or indirectly electrically stimulated. The intraesophageal electrostimulator 100 may include three or more stimulating electrodes. With this configuration, the spinal cord Sp can be electrically stimulated with an arbitrary stimulating electrode.

In the above-described embodiment, the stimulator body 101 has the flexibility also in the width direction perpendicular to the longitudinal direction. With this configuration, the intraesophageal electrostimulator 100 is flexibly deformable along the inner shape of the esophagus S. Thus, the intraesophageal electrostimulator 100 can be smoothly inserted or removed. However, the stimulator body 101 may only be required to have such flexibility that the stimulator body 101 is elastically bendable at least in the longitudinal direction.

In the above-described embodiment, the outer edge portions 102c of the stimulator body 101 at both ends in the width direction have the flexibility. With this configuration, the outer edge portions 102c of the stimulator body 101 deform along the inner wall surface of the esophagus S. Thus, the stimulator body 101 of the intraesophageal electrostimulator 100 can be smoothly inserted. Moreover, the outer edge portions 102c of the stimulator body 101 of the intraesophageal electrostimulator 100 expand the esophagus S into the tubular shape by pushing the inner wall surface of the esophagus S. With this configuration, other medical tools can be easily inserted. However, the stimulator body 101 may have flexibility across the entire area in the width direction. However, the stimulator body 101 may have flexibility only on one end side in the width direction. Alternatively, the stimulator body 101 does not necessarily have the flexibility in the width direction.

Figure 6:
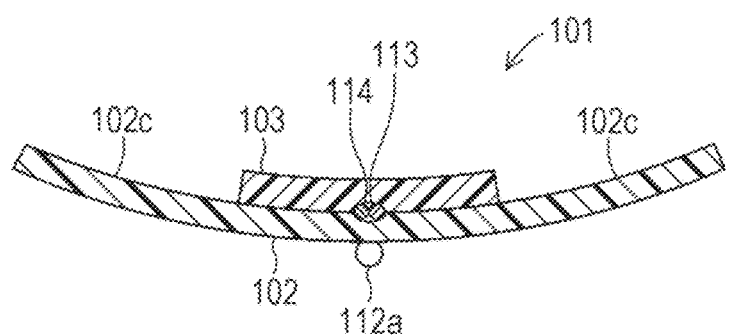
FIG. 6 is a sectional view of a main portion showing an internal configuration of an intraesophageal electrostimulator according to a modification of the present invention.

In the above-described embodiment, the stimulator body 101 is formed in the planar shape extending flat in the longitudinal direction and the width direction. However, the stimulator body 101 may be formed of a flat plate originally formed in a shape bent or curved in the longitudinal direction and/or the width direction. For example, as shown in FIG. 6, the stimulator body 101 may be curved in a downwardly-raised shape as viewed in the figure along the width direction such that the stimulating electrodes 111, 112 project therefrom. According to this configuration, the stimulating electrodes 111, 112 of the intraesophageal electrostimulator 100 can more effectively contact the inner wall surface of the esophagus S. Note that in FIG. 6, the exterior body 104 is also not shown.

In the above-described embodiment, in the stimulator body 101, the second flat plate member 103 is bonded to the center portion of the first flat plate member 102 in the width direction thereof. With this configuration, the stimulator body 101 is formed such that the stiffness of an inner portion between the outer edge portions 102c at both ends in the width direction is higher than the stiffness of the outer edge portion 102c. Thus, buckling (bending in the longitudinal direction) of the stimulator body 101 when the stimulator body 101 is inserted into the esophagus S is reduced. Consequently, the intraesophageal electrostimulator 100 can be smoothly inserted. However, the stimulator body 101 may be formed such that the stiffness of the inner portion between the outer edge portions 102c at both ends in the width direction is equal to or lower than the stiffness of the outer edge portion 102c.

In the stimulator body 101, the thickness of the center portion of the first flat plate member 102 may be greater than the thickness of the outer edge portion 102c. With this configuration, the stimulator body 101 can also be formed such that the stiffness of the inner portion between the outer edge portions 102c is higher than that of the outer edge portion 102c. In the stimulator body 101, a material (e.g., different material having a stiffness higher than that of the first flat plate member 102) different from that of the first flat plate member 102 may be bonded to the center portion in the width direction. With this configuration, the stimulator body 101 can also be formed such that the stiffness of the inner portion between the outer edge portions 102c is higher than that of the outer edge portion 102c.

In the above-described embodiment, the stimulator body 101 is formed in a bullet shape as viewed in plane so as to have the width decreasing from the back end portion 102b side to the tip end portion 102a of the stimulator body 101. With this configuration, the stimulator body 101 of the intraesophageal electrostimulator 100 can be smoothly inserted into the esophagus S. However, the stimulator body 101 may be formed with the same width from the back end portion 102b to the tip end portion 102a of the stimulator body 101. Alternatively, the stimulator body 101 may be formed with the width increasing from the back end portion 102b to the tip end portion 102a.

In the above-described embodiment, the power feed lines 113, 114 are sandwiched by the first flat plate member 102 and the second flat plate member 103. With this configuration, the stimulator body 101 embeds the power feed lines 113, 114. Thus, in the intraesophageal electrostimulator 100, the power feed lines 113, 114 are attached, without separation, integrally with the stimulator body 101. Consequently, the stimulator body 101 can be smoothly inserted into the esophagus S. In addition, other medical tools are easily inserted into the esophagus S. However; in the stimulator body 101, the power feed lines 113, 114 are not necessarily bonded to the first flat plate member 102 and the second flat plate member 103. The power feed lines 113, 114 may be provided in a physically-separated state. The power feed line 113, 114 may be a flat flexible cable having flexibility other than the linear electric wire.

In the above-described embodiment, each of the stimulating electrodes 111, 112 is formed so as to protrude from the plate surface of the stimulator body 101. With this configuration, each of the stimulating electrodes 111, 112 of the intraesophageal electrostimulator 100 can effectively contact the inner wall surface of the esophagus S. However, the stimulating electrodes 111, 112 do not necessarily protrude from the plate surface of the stimulator body 101. The stimulating electrodes 111, 112 may be formed flush with the plate surface. The stimulating electrode 111, 112 may be formed, other than the spherical shape, in a flat plate or film shape or in the shape of a layer containing an evaporated conductive material.

Figure 7:
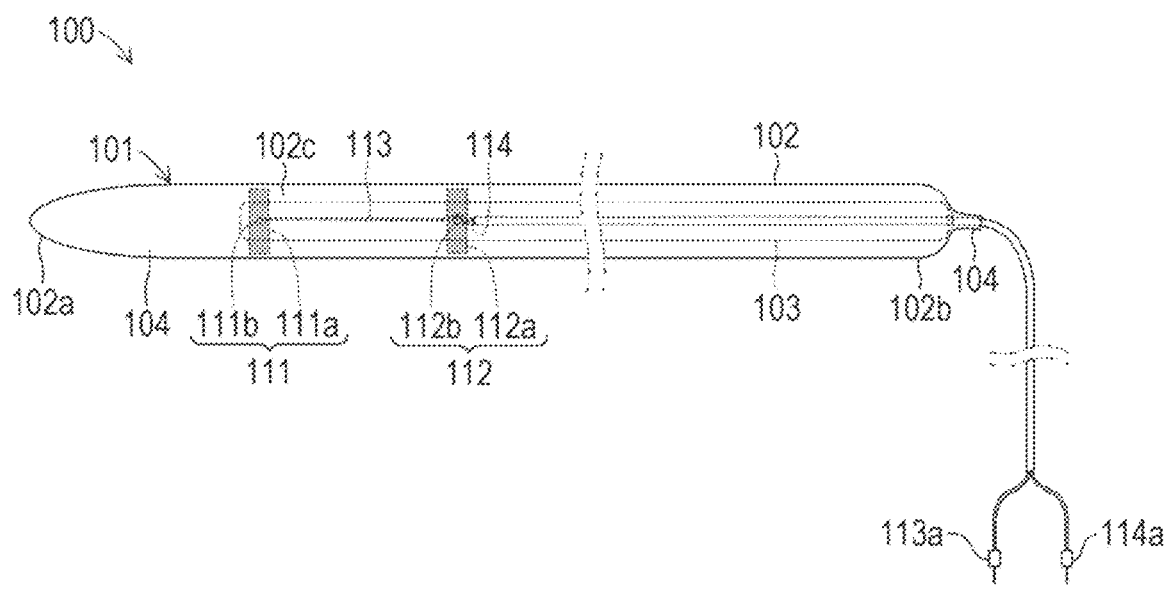
FIG. 7 is a plan view for describing the outline of an external configuration of an intraesophageal electrostimulator according to another modification of the present invention.

As shown in FIG. 7, the stimulating electrode 111, 112 may be configured so as to extend in a planar shape in the width direction of the first flat plate member 102 and surface-contact the inner wall surface of the esophagus S. Note that in FIG. 7, the sheet-shaped, film-shaped, or layer-shaped stimulating electrodes 111, 112 formed so as to extend in a band shape are shaded.

In the above-described embodiment, the stimulator body 101 is formed with a length of 300 mm, a width of 16 mm, and a thickness of 1.2 mm. However, the dimensions of each portion of the stimulator body 101 may be set as necessary according to the size or length of the lumen targeted for insertion. Thus, the dimensions of each portion of the stimulator body 101 are not limited to those of the above-described embodiment, needless to say.

In the above-described embodiment, the stimulator body 101 is entirely covered with the exterior body 104 with the second flat plate member 103 overlapping with the first flat plate member 102. However, the stimulator body 101 may only be required to be formed in the flat plate shape with the flexibility in the longitudinal direction. Thus, the stimulator body 101 may include only the first flat plate member 102. Alternatively, the stimulator body 101 may be formed without covered with the exterior body 104.

For the first flat plate member 102 and the second flat plate member 103, a resin material other than polycarbonate resin, such as flexible polyvinyl chloride resin, polypropylene resin, polyamide resin, polyethylene resin, ABS resin, or polystyrene resin, may be used. Alternatively, the first flat plate member 102 and the second flat plate member 103 may be made of a translucent or opaque material other than the transparent material. The exterior body 104 may be made of a material other than silicon rubber, such as various resin materials.

Figure 8:
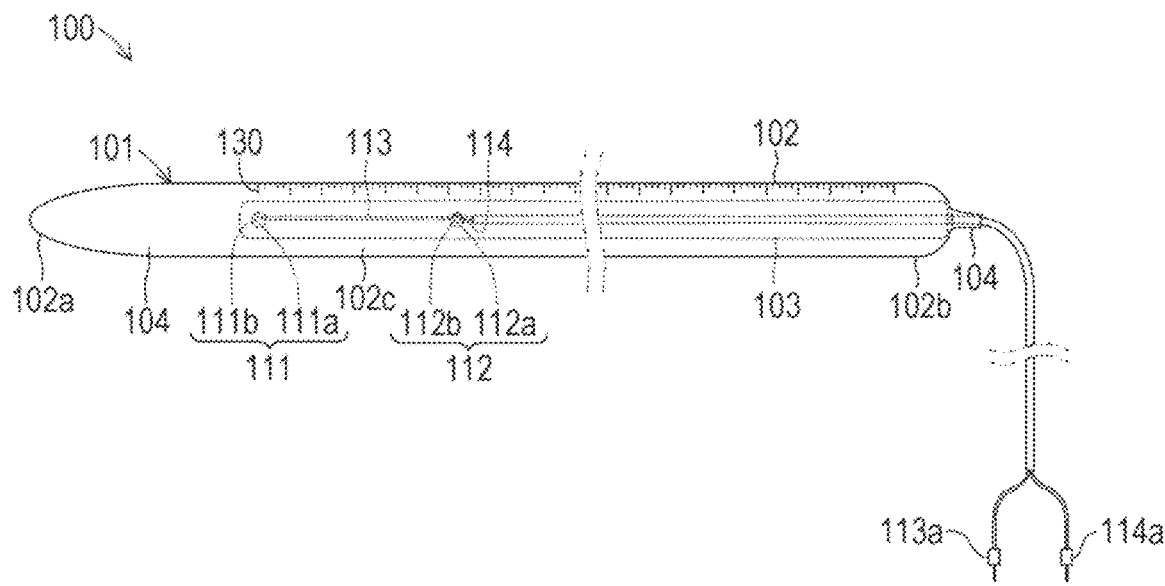
FIG. 8 is a plan view for describing the outline of an external configuration of an intraesophageal electrostimulator according to still another modification of the present invention.

As shown in FIG. 8, the stimulator body 101 may include a scale 130 along the longitudinal direction. According to this configuration, for the intraesophageal electrostimulator 100, the amount of insertion of the stimulator body 101 into the body or the positions of the stimulating electrodes 111, 112 inserted into the body can be correctly grasped with the scale 130. In this case, the scale 130 may indicate a length from the tip end portion 102a of the stimulator body 101. Alternatively, the scale 130 may indicate a length from the stimulating electrode 111 or the stimulating electrode 112. The scale 130 may be formed on the surface of the exterior body 104 by, e.g., printing. Alternatively, the scale 130 may be formed on the surface of the first flat plate member 102 or the second flat plate member 103 covered with the exterior body 104 by, e.g., printing.

In the above-described embodiment, the contact portions 111a, 112a are provided on the plate surface of the first flat plate member 102 opposite to the plate surface to which the second flat plate member 103 is bonded. That is, the stimulating electrodes 111, 112 are provided on the surface of the stimulator body 101 facing the spinal cord Sp in the esophagus S. With this configuration, the intraesophageal electrostimulator 100 can accurately and stably electrically stimulate the spinal cord Sp. However, the stimulating electrodes 111, 112 are not necessarily provided on the surface of the stimulator body 101 facing the spinal cord Sp in the esophagus S as long as the stimulating electrodes 111, 112 can contact the inner wall surface of the esophagus S to electrify the inner wall surface. Thus, the stimulating electrodes 111, 112 may be provided, for example, at least on one of two side surfaces (surfaces of the stimulator body 101 in the thickness direction thereof) of the stimulator body 101. Alternatively, the stimulating electrodes 111, 112 may be provided on both the two plate surfaces of the stimulator body 101. With this configuration, an effort of considering the orientation of the plate surface when the stimulator body 101 is inserted into the esophagus S can be eliminated.

In the above-described embodiment, the entire surface of the stimulator body 101 other than the contact portions 111a, 112a, such as the plate surface on which the stimulating electrodes 111, 112 are provided, the opposite surface thereof, and the two side surfaces, is covered with the exterior body 104. With this configuration, the entire surface of the stimulator body 101 is formed as a smooth surface. Thus, for the intraesophageal electrostimulator 100, friction resistance upon insertion into the esophagus S or removal from the esophagus S can be reduced. Consequently, the stimulator body 101 can be smoothly taken in or out. In addition, other medical tools can also be smoothly taken in or out. Of the stimulator body 101, only any of the plate surface on which the stimulating electrodes 111, 112 are provided, the opposite surface thereof, and the two side surfaces may be formed, however, as a smooth surface. In this case, it is preferable that the plate surface of the stimulator body 101 on which the stimulating electrodes 111, 112 are provided or the opposite surface thereof is formed as a smooth surface. Of the stimulator body 101, a non-smooth one of the plate surface on which the stimulating electrodes 111, 112 are provided, the opposite surface thereof, and the two side surfaces may be formed as a surface having fine asperities, such as a pearskin finish surface. With this configuration, the friction resistance in the esophagus S can be improved, and misalignment and the like can be reduced.

In the above-described embodiment, the intraesophageal electrostimulator 100 is arranged in the esophagus S of the human H. However, the intraesophageal electrostimulator 100 may also be used for a biological body other than the human H, such as animals including, for example, pets such as dogs and cats and livestock such as cows, horses, and pigs.

LIST OF REFERENCE SIGNS

H Human
S Esophagus
M Mouth
N Throat
Sp Spinal Cord
100 Intraesophageal Electrostimulator
101 Stimulator Body
102 First Flat Plate Member
102a Tip End Portion
102b Back End Portion
102c Outer Edge Portion
103 Second Flat Plate Member
104 Exterior Body
111, 112 Stimulating Electrode
111a, 112a Contact Portion
111b, 112b Connection Portion
113, 114 Power Feed Line
113a, 114a Connection Terminal
120 Control Device
121 Operation Board
130 Scale

The invention claimed is:

1. An intraesophageal electrostimulator configured to be arranged in an esophagus to electrically stimulate a spinal cord via an inner wall surface of the esophagus, comprising:
   at least one stimulating electrode that is configured to be arranged in the esophagus to electrically stimulate the inner wall surface of the esophagus;
   a stimulator body that is formed elongated at least with a length from a mouth to a throat and holds the stimulating electrode; and
   a power feed line that supplies electricity to the stimulating electrode,
   wherein the stimulator body is formed in a flat plate shape having a length at least from the mouth to the throat, having flexibility at least in a longitudinal direction, and further having a width that expands a lumen of the esophagus outward,
   the stimulating electrode is provided at a center portion in the width direction of the stimulator body, and
   the stimulator body includes a first flat plate member formed in a flat plate shape, and a second flat plate member formed in a flat plate shape having a narrower width than that of the first flat plate member and overlapping with the first flat plate member.

2. The intraesophageal electrostimulator according to claim 1, wherein
   the stimulator body has flexibility also in a width direction perpendicular to the longitudinal direction.

3. The intraesophageal electrostimulator according to claim 2, wherein
   the stimulator body has flexibility at outer edge portions at both ends in the width direction.

4. The intraesophageal electrostimulator according to claim 3, wherein
   the stimulator body is formed such that a stiffness of an inner portion between the outer edge portions at the both ends in the width direction is higher than a stiffness of each outer edge portion.

5. The intraesophageal electrostimulator according to claim 1, wherein
   the stimulator body is formed with a width decreasing toward a tip portion.

6. The intraesophageal electrostimulator according to claim 5, wherein
   the flat plate shape of the stimulator body before the stimulator body is elastically deformed has a width decreasing toward a tip end portion.

7. The intraesophageal electrostimulator according to claim 5, wherein
   a width of the tip end portion before the stimulator body is elastically deformed is the smallest among all of widths of the stimulator body before the stimulator body is elastically deformed.

8. The intraesophageal electrostimulator according to claim 1, wherein
   the power feed line is attached integrally with the stimulator body.

9. The intraesophageal electrostimulator according to claim 1, wherein
   the stimulating electrode includes at least two stimulating electrodes provided along the longitudinal direction of the stimulator body.

10. The intraesophageal electrostimulator according to claim 1, wherein
    the stimulating electrode protrudes from a plate surface of the stimulator body.

11. The intraesophageal electrostimulator according to claim 1, wherein
    the stimulator body is provided with a scale along the longitudinal direction.

12. The intraesophageal electrostimulator according to claim 1, wherein
    the stimulating electrode is provided on a surface of the stimulator body facing a spinal cord in the esophagus.

13. The intraesophageal electrostimulator according to claim 1, wherein
    the stimulator body is configured such that the stimulating electrode is provided on one surface and the other surface is formed as a smooth surface.

* * * * *